United States Patent [19]

Potts

[11] 4,372,311

[45] Feb. 8, 1983

[54] DISPOSABLE ARTICLES COATED WITH DEGRADABLE WATER INSOLUBLE POLYMERS

[75] Inventor: James E. Potts, Bernards Township, Morris County, N.J.

[73] Assignee: Union Carbide Corporation, Danbury, Conn.

[21] Appl. No.: 186,429

[22] Filed: Sep. 12, 1980

[51] Int. Cl.$^3$ ..................... A61L 15/00; A61F 13/16; B32B 23/08
[52] U.S. Cl. .................... 128/287; 128/156; 428/332; 428/507
[58] Field of Search .................. 128/284, 287, 290 R, 128/296, 156, 285, 260; 260/17.4 GC; 428/332, 334, 507, 500, 508

[56] References Cited

U.S. PATENT DOCUMENTS

| | | | |
|---|---|---|---|
| 3,078,849 | 2/1963 | Morse | 128/290 R |
| 3,197,332 | 7/1965 | Champ . | |
| 3,559,650 | 2/1971 | Larson | 128/290 R |
| 3,651,809 | 3/1972 | Champaigne, Jr. | 128/290 R |
| 3,783,872 | 1/1974 | King . | |
| 3,952,347 | 4/1976 | Comerford et al. | 128/287 |
| 3,957,605 | 5/1976 | Assarsson et al. . | |
| 4,148,871 | 4/1979 | Pitt et al. | 128/260 |
| 4,190,563 | 2/1980 | Bosley et al. | 128/296 |

*Primary Examiner*—C. Fred Rosenbaum
*Attorney, Agent, or Firm*—Donald M. Papuga

[57] ABSTRACT

Described herein are disposable articles made from a water soluble polymer or a substrate made from such polymer, a surface of said article or substrate coated with a degradable water-insoluble polymer.

22 Claims, No Drawings

DISPOSABLE ARTICLES COATED WITH DEGRADABLE WATER INSOLUBLE POLYMERS

BACKGROUND OF THE INVENTION

This invention is directed to disposable articles made from a water soluble polymer, a surface of said article coated with a degradable water-insoluble polymer. The disposable articles include diapers; catamenial devices, such as tampons and applicator tubes for tampons, and sanitary napkins; hospital bed liners; bandages, and the like. Additionally, where an article is subject to outdoor exposure, the article made from the water soluble polymer is coated with the degradable water-insoluble polymer which provides moisture protection for the water soluble polymer until the degradable polymer becomes embrittled by, for example, photo-oxidative degradation. Additionally, such an article, if buried underground, may be biodegraded by microorganisms such as molds, bacterial, etc. Such articles are useful as tapes which contain seeds, carriers for fertilizers, fungicides, pesticides, and the like.

Further, the present invention is directed to a disposable substrate, in the form of, for example, a sheet or film, made from a water soluble polymer, a surface of said substrate coated with a degradable water-insoluble polymer. Such a disposable substrate may be used to contain a liquid or to contain absorbent materials, etc.

Disposable absorbent articles made from water soluble polymers are well known. U.S. Pat. No. 3,783,872, for example, crosslinks an aqueous solution of a poly(ethylene oxide) homopolymer to a hydrophilic water-insoluble poly(ethylene oxide) polymer by utilizing ionizing radiation. These polymers, as stated in U.S. Pat. No. 3,783,872, possess the ability to incorporate large amounts of water and are insoluble in water, irrespective of temperature, and retain liquids, solutions and suspensions.

Additionally, U.S. Pat. No. 3,957,605 cocrosslinks poly(ethylene oxide) and at least one other water soluble polymer by exposing aqueous systems of the polymers to high energy irradiation. The resulting products are insoluble hydrophilic gels which can contain, or when dried, absorb large quantities of aqueous fluids and are useful for absorbing media for disposable absorbent articles such as diapers, sanitary napkins, and the like.

However, since the products are insoluble they cannot be conveniently disposed of into, for example, waste water systems, since they do not disolve therein.

If the disposable article is made from a water soluble polymer, such as poly(ethylene oxide), its utility, in most cases, is limited to application where it will not be in contact with a liquid medium. Due to the water sensitivity of the polymer, even casual contact with moisture will cause the surface of the article to become tacky or slippery, which interferes with the proper function of the article.

Thus, there exists a need to treat the disposable article made from the water soluble polymer to decrease its water sensitivity, yet not render it water insoluble, so that it can be conveniently disposed of into, for example, waste water systems.

U.S. Pat. No. 3,197,332 describes a method for rendering films or shaped articles made from polyethylene oxide polymers water-resistant. A sheet of ethylene oxide polymer is coated on one side with a relatively thin coating of a silicon compound. The coated side of the sheet is water resistant, while if water is applied to the other side, the entire sheet will collapse. However, the silicon coating is not degradable and may be objectionable when disposed of into, for example, waste water systems. Also, the silicon coating may be objectionable when in contact with delicate body tissues.

THE INVENTION

It has now been found that when a surface of a disposable article, made from a water soluble polymer, is coated with a degradable water-insoluble polymer, such a coated article may be readily disposed of into, for example, a waste water system.

A side of the disposable article which is in contact with moisture and/or body tissue is coated with a thin coating of the degradable water-insoluble polymer. The coated side of the article is water resistant, while if water is applied to the other side, the water-soluble polymer will dissolve leaving a thin layer of the degradable water-insoluble polymer which was the coating. Such a coated disposable article finds utility in diapers, catamenial devices, such as tampons, applicator tubes for tampons, and sanitary napkins, hospital bed liners, bandages, and the like.

Additionally, the entire article may be coated with the degradable water-insoluble polymer. This provides moisture protection for the water soluble polymer. The degradable water-insoluble polymer then begins to degrade from its environment, i.e., sunlight, or if buried underground from molds, bacteria, etc. Such degradation of the water-insoluble polymwer permits the water-soluble polymer to dissolve. Further, a substrate such as a sheet or film may be coated on both sides with the degradable water-insoluble polymer. Also, a composite or laminate may be made wherein a thin sheet of the water-insoluble polymer is laminated to a sheet of a water-soluble polymer on either one or both sides. Such a laminate or composite can be used to encase other materials, such as absorbent materials. The applications for such a system includes tapes and coatings for seeds. carriers for organic materials, such as fertilizer, fungicides, pesticides, and the like.

The water soluble polymer which may be used herein is selected from one or more of a poly(alkylene oxide), hydroxyethyl cellulose, hydroxypropyl cellulose, polyvinyl alcohol, polyvinyl pyrrolidone, polyacrylamide, polyacrylic acid, and poly(vinyl methyl ether-co maleic anhydride).

The poly(ethylene oxide) polymers are preferred. They are prepared by methods well known in the art and as found in, for example, U.S. Pat. No. 3,417,064. The poly(ethylene oxide) polymers suitable for use herein include interpolymers and copolymers. The copolymers of ethylene oxide are prepared by reacting ethylene oxide and other components, such as oxirane compounds, i.e., styrene oxide, propylene oxide or butylene oxide, and the like. These copolymers are prepared using various ionic catalysts well known in the art.

Interpolymers of poly(ethylene oxide) are prepared by co-polymerizing poly(ethylene oxide) with one or more vinyl monomers as described in U.S. Pat. No. 3,763,277, by the methods as described therein. These monomers include N,N-dimethylaminoethyl methacrylate, styrene, methyl methacrylate, 2-methyl-5-vinyl pyridine, acrylonitrile, hydroxyethyl methacrylate, acrylic acid, acrylamide, and the like.

The degradable water-insoluble polymer which may be used is selected from one or more of a cyclic ester polymer, a poly(β-hydroxy butyrate), dialkanoyl polymers, such as polyesters and polyurethanes derived from aliphatic polyols, and ethylene polymers.

The cyclic ester polymers are characterized by the following recurring structural linear Unit I:

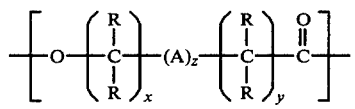
(I)

wherein each R, individually, is selected from the class consisting of hydrogen, alkyl, halo and alkoxy; A is the oxy group; x is an integer from 1 to 4; y is an integer from 1 to 4; z is an integer of zero or one; with the provisos that (a) the sum of $x+y+z$ is at least 4 and not greater than 7, and (b) the total number of R variables which are substituents other than hydrogen does not exceed 3, preferably does not exceed 2, per unit. Illustrative R variables include methyl, ethyl, isopropyl, n-butyl, sec-butyl, t-butyl, hexyl, chloro, bromo, iodo, methoxy, ethoxy, n-butoxy, n-hexoxy, 2-ethylhexoxy, dodecoxy, and the like. A desired cyclic ester is characterized by both recurring structural Unit I supra and recurring structural Unit II:

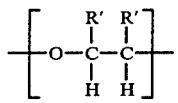
(II)

wherein each R' is selected from the class consisting of, individually, hydrogen, alkyl, cycloalkyl, aryl, and chloroalkyl, and together with the ethylene moiety of the oxyethylene chain of Unit II, a saturated cycloaliphatic hydrocarbon ring having from 4 to 8 carbon atoms, desirably from 5 to 6 carbon atoms. It is preferred that recurring Unit II contains from 2 to 12 carbon atoms.

The aforedescribed recurring linear unit (I) is interconnected through the oxy group (—O—) of one unit with the carbonyl group

of a second unit.

Particularly preferred polymers of cyclic esters are those which are characterized by the oxypentamethylenecarbonyl chain as seen in recurring structural Unit III:

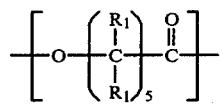
(III)

wherein each $R_1$ is hydrogen or lower alkyl, preferably hydrogen or methyl, with the proviso that no more than three $R_1$ variables are substituents other than hydrogen.

The preparation of the cyclic ester polymers is well documented in the patent literature as exemplified by U.S. Pat. Nos. 3,021,309 through 3,021,317; 3,169,945; and 2,962,524, and Canadian Pat. No. 742,294.

Represented monomeric cyclic esters which are contemplated include, for example, delta-valerolactone; epsiloncaprolactone; zetaenantholactone; etacaprylolactone; the monoalkyldelta-valerolactones, e.g., the monomethyl-, monoethyl-, monohexyl-, delta-valerolactones, and the like.

The preferred cyclic ester polymers are polycaprolactones.

The cyclic ester polymers are well known and are described in, for example, U.S. Pat. No. 3,892,281.

The dialkanoyl polymers are well known in the art and are described in, for example, U.S. Pat. No. 3,850,862, which is incorporated herein by reference.

The dialkanoyl polymers are characterized in that they contain at least about 10 weight percent, preferably greater than about 20 weight percent, of the recurring linear dialkanoyl-containing unit of the formula:

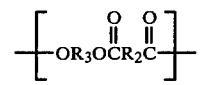

wherein $R_2$ represents a divalent aliphatic hydrocarbon radical desirably a $C_1-C_{12}$ alkylene and $C_2-C_{12}$ alkylidene, e.g., methylene, ethylene, propylene, tetramethylene, heptamethylene, octamethylene, decamethylene, ethylidene, propylidene, octylidene, etc. and wherein $R_3$ represents a divalent aliphatic hydrocarbon radical as described above or a divalent aliphatic oxahydrocarbon radical desirably of the formula $-C_2-C_{12}$ alkylene$<$2-$C_{12}$ alkylene$)_y$.

The normally-solid thermoplastic oxyalkanoyl polymers, on the other hand, are characterized in that they contain at least about 10 weight percent, desirably greater than about 20 weight percent, of the oxyalkanoyl unit.

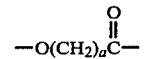

recurring therein, wherein a is an integer having a value of 2, 3, and 5–7, preferably 5.

The aforesaid recurring oxyalkanoyl unit or recurring dialkanoyl unit is interconnected through the oxy group (—O—) of one unit with a carbonyl group

of a second unit. In other words, the interconnection of the oxyalkanoyl units of the dialkonyl unit does not involve the direct bonding of two carbonyl groups

In addition to the apropos recurring unit, the biodegradable thermoplastic polymer may comprise other moieties or groups therein especially those which intersperse or terminate the polymeric chain thereof as illustrated by the

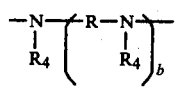

group; the urethane group

the

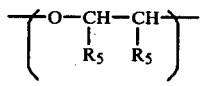

group; the

group; the biuret group,

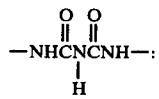

the divalent mono- and polyaromatic rings including fused and bridged rings; lower alkyl substituted oxyalkanoyl groups; catalyst residue; the carbonate group,

and others. In the above illustrated groups, $R_5$ desirably is hydrogen or methyl; y represents an integer which has a value of at least one, e.g., from 1 to 4; and $R_2$ has the aforesaid meaning.

The ethylene polymers are well known in the art and include ethylene homopolymer or copolymer, or a mixture of either or both. The ethylene polymers which are contemplated include those prepared via the polymerization of ethylene, alone, or in admixture with any ethylenically unsaturated monomer, e.g., monomers having the group $>C=C<$, which will copolymerize with ethylene to form normally-solid thermoplastic ethylene copolymers.

The ethylene polymers include the high and low density polyethylenes; ethylene-carbon monoxide copolymers; the ethylene/alkyl 2-alkenoate copolymers such as ethylene/ethyl acrylate copolymer, ethylene/ethyl methacrylate copolymer, etc.; the ethylene/vinyl alkanoate copolymers such as ethyl/vinyl acetate; ethylene methyl vinyl ketone; ethylene/propylene/ethylidenenorbornene copolymer; ethylene/styrene copolymer; and the like. Some of these polymers are used with additives which help degrade the polymer, such as are described in, for example, U.S. Pat. Nos. 3,935,141; 3,901,838; and 3,921,333.

The degradable water-insoluble polymers include those which are biodegradable as well as those which are environmentally degradable.

Biodegradable materials are those which, because of their chemical structure are susceptible to being assimilated by microorganisms such as molds, fungi, and bacteria, when buried in the ground or otherwise contacted with the organisms under conditions conducive to their growth. Accordingly, the term "biodegradable", as used herein, is reserved for that type of degradability which is brought about by living organisms, usually microorganisms. On the other hand, environmentally degradable polymers, such as ethylene polymers are those which by virtue of additives or other material therein are capable of being degraded by the surroundings or environmental elements such as sunlight, rain, moisture, wind, temperature, and the like.

The degradable water-insoluble polymer can be applied to the disposable article made from the water soluble polymer in any convenient manner, such as by dip coating, spray coating, brushing, and the like. While the water-insoluble polymer can be applied directly to the article, a more uniform coating is applied by applying the water-insoluble polymer as a solution in a volatile solvent. Suitable volatile solvents include the saturated and unsaturated hydrocarbon, such as heptane, cyclohexane, toluene and the like; the halogenated hydrocarbons, such as chlorobenzene, chloroform, methylene chloride, and the like; and hydrocarbon alcohols and hydrocarbon alcohol ethers, such as ethylene glycol, propylene glycol, and the like.

The coating of the water-insoluble polymer, whether applied alone or from a solvent, is dried after application. Drying can be accomplished at room temperature or at an elevated temperature.

The water-insoluble polymer is generally applied as a solution containing from about 0.5 to about 10, preferably from about 3 to 10, weight percent of the polymer in a solvent.

The water-insoluble polymer is applied to the article or substrate to achieve a thickness of from about 0.05 to about 5.0 mils thereon.

The water-insoluble polymer may be mixed with other additives prior to coating, such as pigments, dyes, fillers and the like.

EXAMPLES

The following examples serve to give specific illustrations of the practice of this invention but they are not intended in any way to limit the scope of this invention. In these examples, all parts and percentages are on a weight basis unless otherwise specified.

EXAMPLES 1 TO 4

10×10×0.10 inch sheets made from poly(ethylene oxide) [Polyox TM sold by Union Carbide Corporation having a molecular weight of about 40,000] and containing 40 weight percent of calcium carbonate, were coated on one side with a 0.5 mil thick coating of polycaprolactones. Some sheets were coated with a polycaprolactone having a molecular weight of 10,000 and others with a polycaprolactone having a molecular weight of 40,000 by dip coating. The polycaprolactone polymers were dissolved in methylene chloride solvent to the concentrations shown in the Table. The samples were dried at 25° C. for about ten minutes. The sheets were tested for water sensitivity by placing them between two microscope slides, one of which was wetted with water. The wet slide contacted the surface coated with the polycaprolactone. The sample was checked every 30 seconds to test for tackiness.

The results are shown in the Table.

TABLE

| Example | Molecular weight of the Polycaprolactone Polymer | % of Polycaprolactone polymer in solvent | Remarks |
|---|---|---|---|
| 1 | 10,000 | 1 | Tacky after 30 seconds |
| 2 | 10,000 | 3 | Tacky after 30 seconds |
| 3 | 40,000 | 1 | Tacky after 30 seconds |
| 4 | 40,000 | 3 | No tackiness after 30 minutes contact with water. |

The data in the Table show that optimum resistance to moisture resulted from the use of a 3 percemt solution of polycaprolactone polymer in coating the poly(ethylene oxide) sheets.

EXAMPLE 5

A 10×10×0.10 inch sheet made from the poly(ethylene oxide) as described in Examples 1 to 4, and containing 2 percent of calcium carbonate, was coated on one side with a 0.5 mil thick coating of polycaprolactone polymer, having a molecular weight of 40,000, as a 3 percent solution in methylene chloride. The samples were dried at 25° C. for about 10 minutes. The sheet was tested for water sensitivity by placing it between two microscopic slides, one of which was wetted with water. After 30 seconds of contact between the water and the coated surface, the coated surface was not tacky nor did the calcium carbonate smear.

The sample was immersed into 500 ml. of water, at room temperature (about 25° C.), agitated by a magnetic stirrer. After about 5 minutes, the poly(ethylene oxide) sheet had dissolved. A thin film remained. This film was the polycaprolactone coating. The thickness of the film varied from 0.5 to 1.0 mil. This film is biodegradable by both bacteria and fungi such as are found in waste water systems.

EXAMPLE 6

A 10×10×0.10 inch sheet made from the poly(ethylene oxide) as described in Examples 1 to 4 was coated on one side with a one mil sheet of ethylene-carbon monoxide copolymer (DHDA-4164 made by Union Carbide Corporation having an apparent density of 0.939 gms/cc and a melt index of 0.6) by laminating the one mil sheet to the poly(ethylene oxide) sheet.

The composite was cut into one inch wide strips for testing. One strip was exposed to water on the side containing ethylene-carbon monoxide copolymer for one hour. The water had no effect.

The strip was then immersed in water. The poly(ethylene oxide) sheet dissolved completely in about 5 minutes.

Another strip was exposed under an ultraviolet lamp for 25 hours, which caused the ethylene-carbon monoxide copolymer coating to become embrittled. On subsequent contact with water, the embrittled film failed to prevent water from dissolving the poly(ethylene oxide).

This Example demonstrates that the water insoluble polymer can be degraded by ultraviolet light, i.e., sunlight.

EXAMPLE 7

Four of the following water soluble grades of polyvinyl pyrollidone:
(A) Type NP-K-30 (sold by General Aniline & Film Co., New York, New York);
(B) Type NP-K-90 (sold by General Aniline & Film Co.)
(C) Plasdone XL (sold by General Aniline & Film Co.)
(D) No. 1051 having a molecular weight of 40,000 (sold by Polysciences Inc., Warrington, Pa.) were formed into 10×10×0.10 inch sheets by hot pressing above the melting point of the polymer. A coating approximately 0.5 mil thick of polycaprolactone polymer having a molecular weight of 40,000 as a 3 percent solution in methylene chloride was applied to one side of each of the sheets with a camel hair brush. The sheets were dried at room temperature (about 25° C.) for about one hour. The sheets were cut into strips and tested for sensitivity to water by placing one drop of water on the coated side of each strip. After about 10 minutes the strip was not sticky.

The strips were placed into water at room temperature. The poly(ethylene oxide) portion of the strip dissolved in the water leaving a thin film, which was the polycaprolactone coating.

EXAMPLE 8

The procedure of Example 7 was exactly repeated except that a 20 mil sheet of hydroxy ethyl cellulose (Natrosol 250 MBR sold by Hercules Chemical Company) was coated with the polycaprolactone solution.

The coated sheet was tested for sensitivity to water as described in Example 7. After about 10 minutes the strip was not sticky.

The strips were placed into water at about 25° C. The hydroxy ethyl cellulose portion of the strips dissolved in the water leaving a thin film, which was the polycaprolactone coating.

EXAMPLE 9

The procedure of Example 7 was exactly repeated except that a 20 mil sheet of hydroxy propyl cellulose (Klucel sold by Hercules Chemical Company) was coated with the polycaprolactone solution.

The coated sheet was tested for sensitivity to water as described in Example 7. After about 10 minutes, the strip was not sticky.

The strips were placed into water at room temperature. The hydroxy propyl cellulose portion of the strips dissolved in the water leaving a thin film, which was the polycaprolactone coating.

EXAMPLE 10

The four grades of polyvinyl pyrollidone (described in Example 7) were formed into 20 mil thick sheets by the procedure described in Example 7. The sheets were then coated on both sides with a one mil thick sheet of an ethylene-carbon monoxide copolymer (DHDA-4164 described in Example 6) by laminating. The composite so formed was cut into one inch wide strips. Water was placed on one side of the strip. After 30 minutes, there was no evidence of tackiness on the surface.

The strips were then exposed under an ultraviolet lamp for 25 hours. The strip was then immersed in water. The strip became tacky as the water soluble polymer began to leach out of the composite.

EXAMPLE 11

The procedure of Example 10 was exactly repeated except that a 20 mil thick sheet of hydroxy ethyl cellulose (described in Example 8) was coated with the ethylene-carbon monoxide copolymer.

The composite so formed was cut into one inch strips. Water was placed on the side of the strip which was the ethylene-carbon monoxide copolymer. After 30 minutes there was no evidence of tackiness on the surface.

The strip was then exposed under an ultraviolet lamp for 25 hours. The strip was then immersed in water. The strip became tacky as the water soluble polymer began to leach out of the composite.

EXAMPLE 12

The procedure of Example 10 was exactly repeated except that a 20 mil thick sheet of hydroxy propyl cellulose (described in Example 9) was coated with the ethylene-carbon monoxide copolymer.

The composite so formed was cut into one inch strips. Water was placed on the side of the strip which was the ethylene-carbon monoxide copolymer. After 30 minutes, there was no evidence of tackiness on the surface.

The strip was then exposed under an ultraviolet lamp for 25 hours. The strip was then immersed in water. The strip became tacky as the water soluble polymer began to leach out of the composite.

What is claimed is:

1. A disposable article made from a water soluble polymer selected from one or more of a poly(alkylene oxide), hydroxyethyl cellulose, hydroxypropyl cellulose, polyvinyl alcohol, polyvinyl pyrrolidone, polyacrylamide, polyacrylic acid, or poly(vinyl methyl ether-co maleic anhydride), a surface of said article coated with a degradable water-insoluble polymer selected from one or more of a cyclic ester polymer, a poly($\beta$-hydroxy butyrate), a dialkanoyl polymer, or an ethylene polymer.

2. A disposable article as defined in claim 1, wherein the surface of the article is coated with from about 0.05 to about 5.0 mils of the water-insoluble polymer.

3. A disposable article as defined in claim 1 which is a catamenial device.

4. A disposable article as defined in claim 3 which is a sanitary napkin.

5. A disposable article as defined in claim 3 which is a tampon applicator.

6. A disposable article as defined in claim 1 which is a diaper.

7. A disposable article as defined in claim 1 which is a bandage.

8. A disposable article as defined in claim 1, wherein the entire surface of the article is coated with a degradable water-insoluble polymer.

9. A disposable article as defined in claim 8 which is a laminate.

10. A disposable article as defined in claim 8 which contains a seed therein.

11. A disposable article as defined in claim 8 which is a carrier for organic material.

12. A disposable article containing a poly(ethylene oxide) polymer, a surface of the article containing such polymer coated with a degradable water-insoluble polymer.

13. A disposable article as defined in claim 12 wherein the water-insoluble polymer is a biodegradable polycaprolactone polymer.

14. A disposable article as defined in claim 12 which is a catamenial device.

15. A disposable article as defined in claim 14 which is a sanitary napkin.

16. A disposable article as defined in claim 14 which is a tampon applicator.

17. A disposable article as defined in claim 12 or 13 which is a diaper.

18. A disposable substrate made from a water soluble polymer selected from one or more of a poly(alkylene oxide), hydroxyethyl cellulose, hydroxypropyl cellulose, polyvinyl alcohol, polyvinyl pyrrolidone, polyacrylamide, polyacrylic acid, or poly(vinyl methyl ether-co maleic anhydride), a surface of said substrate coated with a degradable water-insoluble polymer is selected from one or more of a cyclic ester polymer, a poly($\beta$-hydroxy butyrate), a dialkanoyl polymer, or an ethylene polymer.

19. A disposable substrate as defined in claim 18 in the form of a film or sheet.

20. A disposable substrate as defined in claim 18, wherein the surface is coated with from about 0.05 to about 5.0 mils of the water-insoluble polymer.

21. A disposable article or substrate made from a water soluble polymer containing a coating on at least one surface thereof, which coating comprises from about 0.05 to about 5.0 mils of a degradable water-insoluble polymer.

22. A disposable article or substrate as defined in claim 21, wherein the water soluble polymer is a poly(ethylene) oxide.

* * * * *